US012622811B2

(12) United States Patent
Jiang et al.

(10) Patent No.: US 12,622,811 B2
(45) Date of Patent: May 12, 2026

(54) INSERTION TOOL FOR AN EYE DISEASE TREATMENT DEVICE

(71) Applicant: Avisi Technologies, Inc., Redwood City, CA (US)

(72) Inventors: Rui Jing Jiang, Lexington, MA (US); Brandon Kao, Placentia, CA (US); Georgia Griggs, Philadelphia, PA (US); Michael Yates, Redwood City, CA (US)

(73) Assignee: Avisi Technologies, Inc., Redwood City, CA (US)

( * ) Notice: Subject to any disclaimer, the term of this patent is extended or adjusted under 35 U.S.C. 154(b) by 303 days.

(21) Appl. No.: 18/555,476

(22) PCT Filed: Apr. 14, 2022

(86) PCT No.: PCT/US2022/024789
§ 371 (c)(1),
(2) Date: Oct. 13, 2023

(87) PCT Pub. No.: WO2022/221518
PCT Pub. Date: Oct. 20, 2022

(65) Prior Publication Data
US 2024/0189146 A1 Jun. 13, 2024

Related U.S. Application Data

(60) Provisional application No. 63/174,883, filed on Apr. 14, 2021.

(51) Int. Cl.
*A61F 9/007* (2006.01)
*A61B 17/30* (2006.01)
(Continued)

(52) U.S. Cl.
CPC .......... *A61F 9/00781* (2013.01); *A61B 17/30* (2013.01); *A61B 90/08* (2016.02); *A61F 9/0017* (2013.01); *A61B 2090/0817* (2016.02)

(58) Field of Classification Search
CPC .... A61F 9/00781; A61F 9/0017; A61F 9/007; A61F 2/1664; A61B 17/0231; A61B 17/30
See application file for complete search history.

(56) References Cited

U.S. PATENT DOCUMENTS

| | | | | | |
|---|---|---|---|---|---|
| 4,844,065 | A | * | 7/1989 | Faulkner | A61B 17/30 606/107 |
| 5,662,659 | A | | 9/1997 | McDonald | |
| 2009/0177138 | A1 | * | 7/2009 | Brown | A61F 9/00781 606/108 |

FOREIGN PATENT DOCUMENTS

WO 2020/150657 A1 7/2020

OTHER PUBLICATIONS

International Search Report and Written Opinion of PCT/US2022/024789, dated Jul. 13, 2022, in 13 pages.

* cited by examiner

*Primary Examiner* — Susan S Su
*Assistant Examiner* — Erin A Kim
(74) *Attorney, Agent, or Firm* — K&L Gates LLP

(57) ABSTRACT

Described herein are insertion tools for inserting a treatment device into a pocket formed between conjunctival tissue and scleral tissue for treating high intraocular pressure and glaucoma. An insertion tool (800) includes a scissoring mechanism or an expandable mechanism that is configured to expand a pocket formed between conjunctival tissue and scleral tissue. The scissoring mechanism or the expandable mechanism is also configured to unfurl a treatment device within the pocket.

20 Claims, 16 Drawing Sheets

(51) Int. Cl.
A61B 90/00          (2016.01)
A61F 9/00          (2006.01)

example cross-section
of scissoring Body insertion device
which VisiPlate is wrapped around delivered in canula which is
extracted to allow movement Scissoring mechanism
spreads Visiplate and
then closes back to <3mm
width. (curved to
follow radius of eye)

needed to spread 6mm wide VisiPlate

3mm incision

INSERTION TOOL FOR AN EYE DISEASE TREATMENT DEVICE

PRIORITY CLAIM

This application is a national phase entry of PCT Application No. PCT/US2022/024789, filed on Apr. 14, 2022, which claims the benefit of U.S. Provisional Application No. 63/174,883, filed on Apr. 14, 2021, the entire disclosure of which are incorporated herein by reference.

BACKGROUND

Millions of individuals suffer from eye disease, specifically glaucoma. Most glaucoma patients have abnormally high intraocular pressure (IOP) due to the patient's inability to drain excessive aqueous humor from the anterior chamber of the eye through the trabecular meshwork. If not reduced with adequate treatment, high IOP will continuously damage the optic nerve as the disease progresses, leading to loss of vision or even total blindness. Current medications, surgeries, and implants have proven inadequate in lowering pressure within the eye or sustaining normal eye pressure over many years. Therefore, a need exists for new ways to alleviate IOP, thereby treating glaucoma.

SUMMARY

Described herein are treatment devices, or simply devices, configured for treating ocular and other conditions. In one embodiment, an ocular condition is elevated intraocular pressure, and the devices herein are configured to lower the intraocular pressure. In another embodiment, a condition is hydrocephalus, and the devices herein are configured to lower pressure. The devices generally include a plate structure or core component comprising a first major surface coated with a first material and a second major surface coated with a second material.

The treatment device disclosed herein is configured for insertion into a subconjunctival pocket of a patient's eye. To reduce scaring and post-operative patient discomfort, it is desired to make as small as incision of the conjunctiva as possible, ideally less than 3 millimeters ("mm"). However, the treatment device, in many embodiments, has a width between 3 and 10 millimeters, preferably around 5 mm to provide to adequate drainage of aqueous humor from an anterior chamber of a patient's eye. This means that the treatment device is wider than a desired incision width.

To enable insertion, the treatment device is folded or furled around an insertion device. After the insertion device passes through the conjunctiva incision, the insertion device is configured to unfold or unfurl the treatment device so that it rests flat or nearly flat within the subconjunctival pocket. In some embodiments, the example insertion device disclosed herein includes an expandable or scissoring mechanism with flat (overlapping) ends. After insertion, the expandable mechanism may be squeezed or the scissoring mechanism may be rotated, thereby causing the flat ends to separate and unfurl the treatment device within the subconjunctival pocket. In other embodiments, the insertion tool may include a forceps inserter that slides a furled treatment device in place, and then uses broad prongs to unfurl or flatten the treatment device. In yet other embodiments, a blunt tool having a width less than a width of the conjunctiva incision is used to unfurl the treatment device after insertion by another tool, such as tweezers or a needle/syringe (via an injection method).

Other embodiments include methods of reducing intraocular pressure. In one embodiment, a method includes securing the treatment device as described herein to an eye thereby moving ocular fluids and reducing intraocular pressure.

In some embodiments, the plate structure is formed of a ceramic material. The ceramic material can be selected from aluminum oxide (alumina), silicon nitride, silica, hafnium oxide, titanium nitride, titanium, or combinations thereof.

In some embodiments, the first coating is a polymeric material. The polymeric material can be a parylene polymer. The parylene polymer can be parylene C, parylene D, parylene N, a derivative thereof or a combination thereof.

In other embodiments, the polymeric material includes rubber, synthetic rubber, silicone polymers, parylene, thermoplastics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides such as PLA, PLGA, PLLA, derivatives thereof, or combinations thereof.

In some embodiments, the second coating includes aluminum oxide and/or a parylene polymer.

In some embodiments, the second coating includes aluminum oxide in combination with rubber, synthetic rubber, silicone polymers, parylene, thermoplastics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides such as PLA, PLGA, PLLA, derivatives thereof, or combinations thereof.

The series of fluid channels can include a plurality of open-ended channels interconnected to form an intersecting network (or grid pattern) of fluid pathways. In some embodiments, the channels are microchannels.

In some embodiments, treating the high intraocular pressure is a treatment for glaucoma.

In some embodiments, treating the high intraocular pressure is a treatment for glaucoma.

In light of the disclosure set forth herein, and without limiting the disclosure in any way, in a first aspect of the present disclosure, which may be combined with any other aspect, or portion thereof, described herein a system for lowing intraocular pressure includes an insertion tool comprising a first arm connected to a second arm at a pivot point forming a scissoring mechanism, a first prong connected to a first end of the first arm, and a second prong connected to a first end of the second arm. The first and second prongs are configured to have a combined dimension that is less than a length of an incision of conjunctival tissue of a patient's eye when the first and second arms are in a closed position. The first and second arms are configured to be actuated to an open position after the first and second prongs are inserted into a pocket formed between the conjunctival tissue and scleral tissue of the patient's eye. Actuation to the open position causes the first and second prongs to separate and increase a width of the pocket. The system additionally includes a treatment device configured to furl or wrap around the first and second prongs when the first and second arms are in a closed position. The first and second prongs are configured to cause the treatment device to unfurl or spread to a flat shape in the pocket when the first and second arms are actuated to the open position.

In a second aspect of the present disclosure, which may be combined with any other aspect, or portion thereof, described herein, the first and second prongs have at least a flat side to spread out the treatment device to the flat shape.

In a third aspect of the present disclosure, which may be combined with any other aspect, or portion thereof, described herein, the first and second prongs are configured to at least one of overlap or interlock when the when the first and second arms are in the closed position.

In a fourth aspect of the present disclosure, which may be combined with any other aspect, or portion thereof, described herein, the treatment device includes a foldable plate comprising a first surface opposite a second surface, wherein the first surface includes a series of fluid channels, a first coating on the first surface, and a second coating on the second surface. The fluid channels form a geometric pattern with each channel having a height and first width to produce a desired fluid flow rate.

In a fifth aspect of the present disclosure, which may be combined with any other aspect, or portion thereof, described herein, the foldable plate includes an extension portion for placement within an anterior chamber of the patient's eye, and the fluid channels include a plurality of open-ended channels interconnected to form an intersecting network of fluid pathways.

In a sixth aspect of the present disclosure, which may be combined with any other aspect, or portion thereof, described herein, the first and second prongs have at least one of a radiused edge or a blunted leading edge.

In a seventh aspect of the present disclosure, which may be combined with any other aspect, or portion thereof, described herein, the first and second prongs are shaped to match a shape of the unfurled foldable plate.

In an eighth aspect of the present disclosure, which may be combined with any other aspect, or portion thereof, described herein, the first and second prongs are configured to expand to a predefined geometry that is greater than a surface of the unfurled foldable plate.

In a ninth aspect of the present disclosure, which may be combined with any other aspect, or portion thereof, described herein, a cannula is provided over the first and second prongs to retain the furled treatment device during insertion into the pocket formed between the conjunctival tissue and scleral tissue of the patient's eye.

In a tenth aspect of the present disclosure, which may be combined with any other aspect, or portion thereof, described herein, the system further includes a first handle connected to a second end of the first prong and a second handle connected to a second end of the second prong.

In an eleventh aspect of the present disclosure, which may be combined with any other aspect, or portion thereof, described herein, an insertion tool for a device that lowers intraocular pressure comprises a first arm having a first end and a second end, and second arm having a first end and a second end. The second end of the second arm is connected to or integrally formed with the second end of the first arm. The first arm and the second arm are bent or angled with respect to each other forming an expandable mechanism such that a first end of the first arm contacts the first end of the second arm when external force is absent. The first ends of the first and second arms are configured to have a combined dimension that is less than a length of an incision of conjunctival tissue of a patient's eye when the first and second arms are in a closed position. Additionally, the first and second arms are configured to be actuated to an open position after the first ends of the first and second arms are inserted into a pocket formed between the conjunctival tissue and scleral tissue of the patient's eye, wherein actuation to the open position causes the first ends to separate and increase a width of the pocket.

In a twelfth aspect of the present disclosure, which may be combined with any other aspect, or portion thereof, described herein, the first end of the first arm and the first end of the second arm include flat surfaces.

In a thirteenth aspect of the present disclosure, which may be combined with any other aspect, or portion thereof, described herein, a treatment device is furled or wrapped around the first and second ends when the first and second arms are in a closed position, and the first and second ends are configured to cause the treatment device to unfurl or spread to a flat shape in the pocket when the first and second arms are actuated to the open position.

In a fourteenth aspect of the present disclosure, which may be combined with any other aspect, or portion thereof, described herein, the treatment device includes a foldable plate comprising a first surface opposite a second surface, wherein the first surface includes a series of fluid channels, a first coating on the first surface, and a second coating on the second surface. The fluid channels form a geometric pattern with each channel having a height and first width to produce a desired fluid flow rate.

In a fifteenth aspect of the present disclosure, which may be combined with any other aspect, or portion thereof, described herein, the first and second arms include a hydrophobic coating.

In a sixteenth aspect of the present disclosure, which may be combined with any other aspect, or portion thereof, described herein, a method of inserting a treatment device to lower intraocular pressure comprises causing the treatment device to wrap around two prongs or ends of an expandable mechanism when the two prongs or ends are in a closed position, causing an incision to be made to conjunctival tissue of a patient's eye, and causing the two prongs to go through the incision forming a pocket between the conjunctival tissue and scleral tissue of the patient's eye, an extension portion of the treatment device protruding from the incision. The method also includes causing the two prongs to separate to an open position and causing a width of the pocket to widen. The method further includes causing the treatment device to unwrap to a flat sheet within the pocket, causing the two prongs to move to the closed position, and causing the two prongs of the expandable mechanism to be removed from the pocket through the incision. A diameter of the two prongs and the wrapped treatment device is less than a diameter of the incision.

In a seventeenth aspect of the present disclosure, which may be combined with any other aspect, or portion thereof, described herein, the method further comprises causing a second incision to be made into the scleral tissue to provide access to an anterior chamber of the patient's eye, and causing the extension portion of the treatment device to be placed into at least a portion of the anterior chamber, thereby forming a fluid pathway between the anterior chamber and the pocket between the conjunctival tissue and scleral tissue of the patient's eye.

In an eighteenth aspect of the present disclosure, which may be combined with any other aspect, or portion thereof, described herein, the method further includes suturing the incision after removal of the two prongs.

In a nineteenth aspect of the present disclosure, which may be combined with any other aspect, or portion thereof, described herein, the method further includes forming at least one suture hole on the treatment device using a laser, and reinforcing the at least one suture hole.

In a twentieth aspect of the present disclosure, which may be combined with any other aspect, or portion thereof, described herein, the method further includes causing tissue glue to be placed within the at least one suture hole, and after the treatment device unwraps, causing the tissue glue to anchor the treatment device to the scleral tissue.

In a twenty-first aspect any of the features, functionality and alternatives described in connection with any one or more of FIGS. 1 to 13 may be combined with any of the features, functionality and alternatives described in connection with any other of FIGS. 1 to 13.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

The present invention will become more fully understood from the detailed description and the accompanying drawings, wherein.

DETAILED DESCRIPTION

Figure 1:
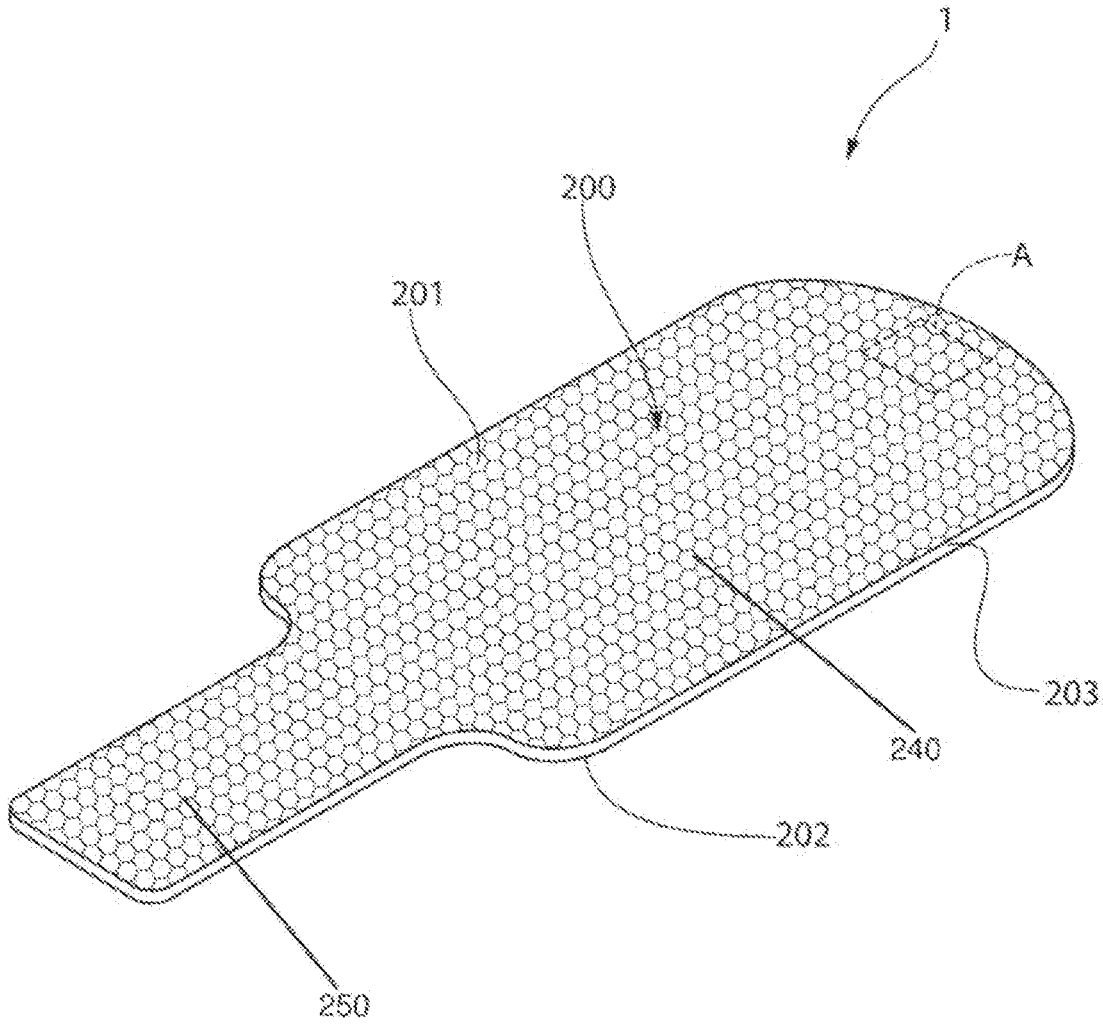
FIG. 1 is a perspective view of a device according to one embodiment.

The following description of the embodiment(s) is merely exemplary in nature and is in no way intended to limit the invention, its application, or uses.

Reference is made herein to lowering intraocular pressure. However, it should be appreciated that the disclosed devices and methods may low fluid pressure of other organs or tissue. For example, the disclosed devices and methods may be used to lower an accumulation of fluid in the brain.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the structure be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the weight of the material. According to the present application, the term "about" means+/−5% of the reference value. According to the present application, the term "substantially free" means less than about 0.1 wt. % based on the total of the referenced value.

A "subject" herein may be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc.

Treatment Device Embodiment

Figure 2:
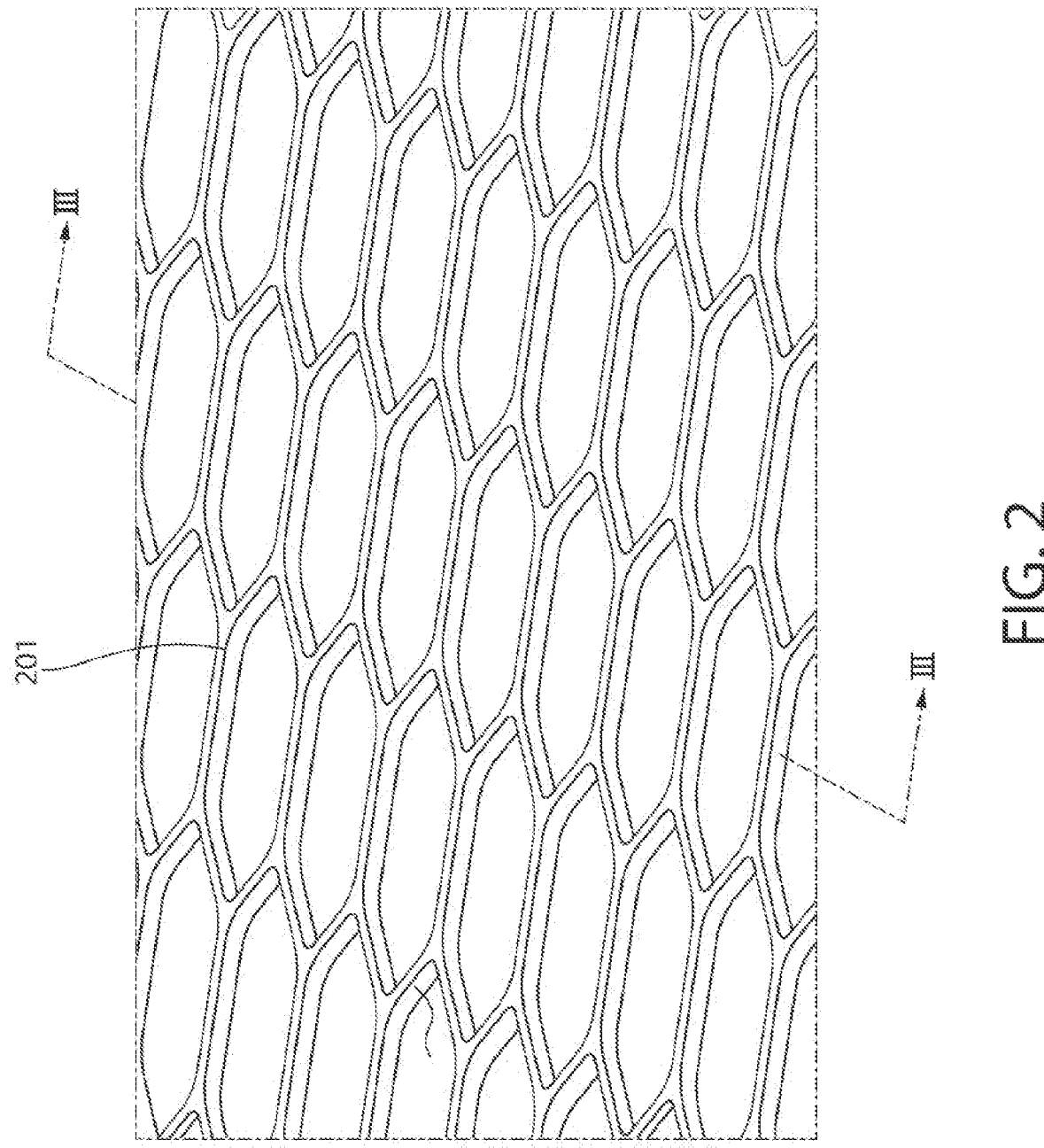
FIG. 2 is a close-up view of the device according to section A identified in FIG. 1.
Figure 3:
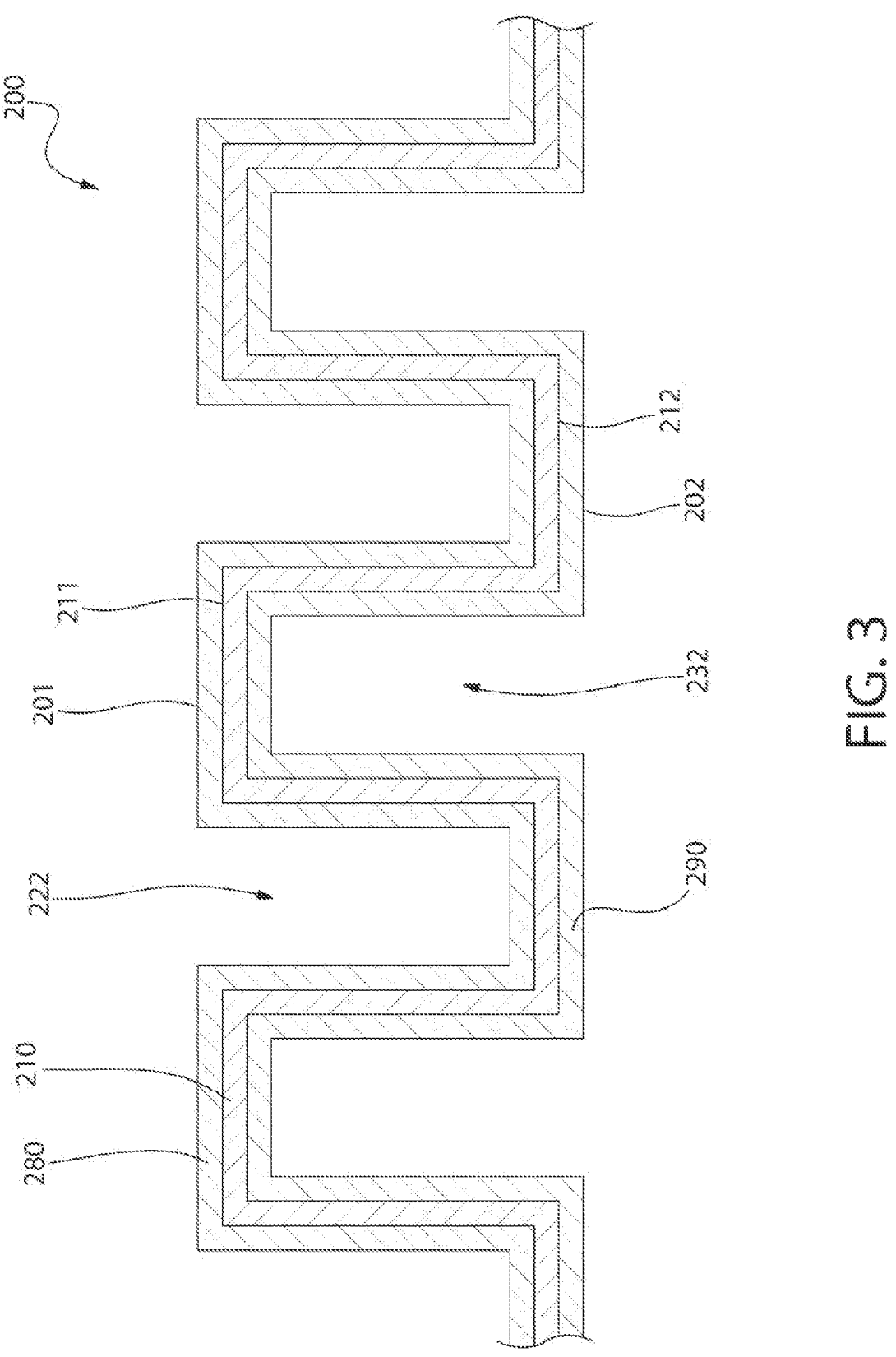
FIG. 3 is a cross-sectional view of the device shown along line III-III in FIG. 2.
Figure 4:
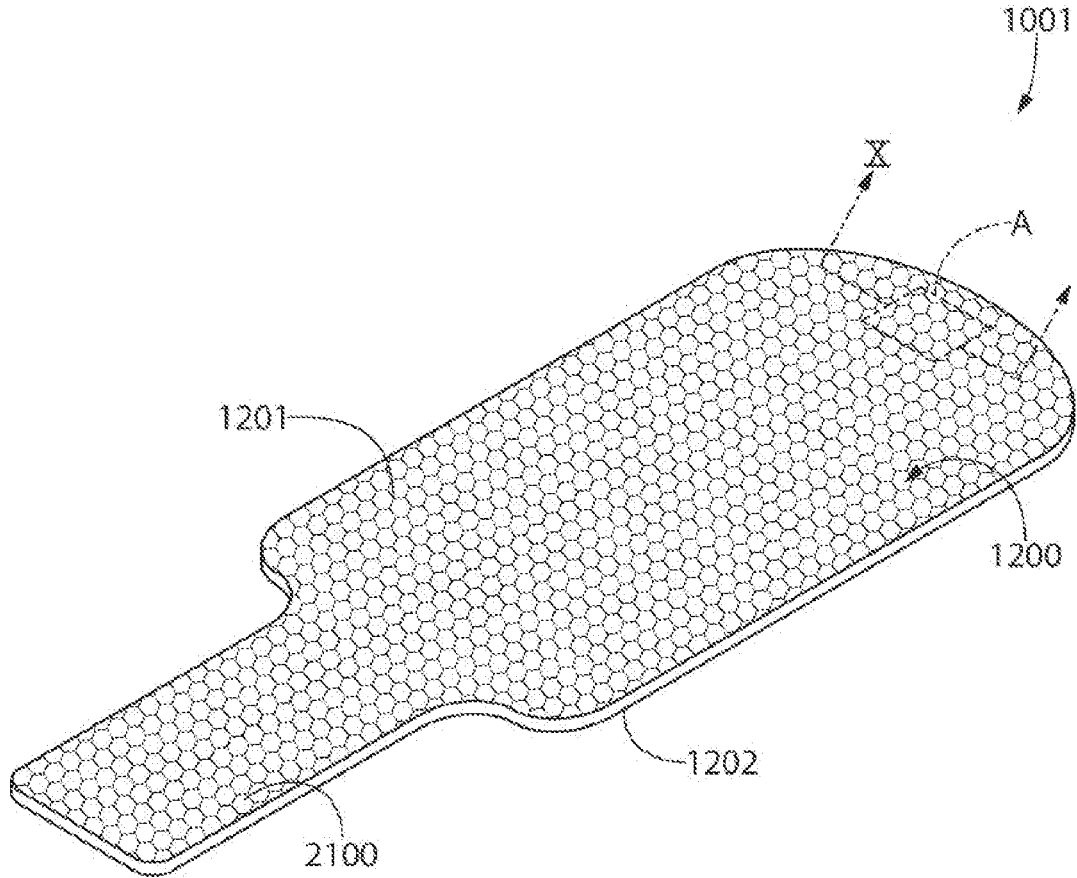
FIG. 4 is a perspective view of a device according to another embodiment.

Referring to FIGS. 1-3, a treatment device 1 includes a plate structure 200, or simply plate, having a first major exposed surface 201 opposite a second major exposed surface 202 as well as side surface 203 extending there-between. The plate structure 200 can comprise an extension portion 250 and a main body portion 240.

The plate structure 200 can be formed of any material with appropriate characteristics for implantation and treatment. In some embodiments, the plate structure 200 can be formed of a metal, polymer, ceramic (e.g., aluminum oxide), other composite material, or a combination thereof. Metals can include, but are not limited to aluminum, titanium, zinc, platinum, tantalum, copper, nickel, rhodium, gold, silver, palladium, chromium, iron, indium, ruthenium, osmium, tin, iridium, or combinations, and alloys thereof. In some embodiments, alloys can include steel and nickel titanium such as Nitinol.

Polymers or polymer materials used to form plate structure 200 can include any of the polymers described herein.

Composites such as silicon composites can also be used. In one embodiment, a composite can include silicon nitride ($Si_3N_4$). The silicon nitride can have any known crystalline structure such as, but not limited to, trigonal $\alpha$-$Si_3N_4$, hexagonal $\beta$-$Si_3N_4$, or cubic $\gamma$-$Si_3N_4$.

The plate structure 200, or plate, can have a thickness ranging from about 1 nm to about 1,000 nm, from about 1 nm to about 500 nm, from about 1 nm to about 400 nm, from about 100 nm to about 1,000 nm, from about 200 nm to about 1,000 nm, from about 300 nm to about 1,000 nm, from about 400 nm to about 1,000 nm, from about 1 nm to about 900 nm, from about 1 nm to about 800 nm, from about 1 nm to about 700 nm, from about 1 nm to about 600 nm, from about 300 nm to about 500 nm, from about 300 nm to about 600 nm, from about 400 nm to about 600 nm, from about 200 nm to about 600 nm, from about 200 nm to about 500 nm, or from about 50 nm to about 800 nm.

The plate structure 200 may comprise a multi-directional plate 210 comprising a first major surface 211 opposite a second major surface 212. The multi-directional plate 210 may form a plurality of topographical features (for example, a repeating honeycomb pattern) on each of the first major surface 211 and the second major surface 212. Each of the first and second topographies may independently comprise a plurality of channels 232 and/or a plurality of open-cells 222.

The plurality of channels 232 may be interconnected and can form a network of channels. The channels may be open or closed, allowing fluid to readily enter each channel of plurality of channels 232 and flow through it. The network may comprise intersecting channels in any suitable configuration to best help promote the flow of fluid across the plate structure 200 via the plurality of channels 232. In one embodiment, the channels 232 may be configured to form hexagonal patterns. Once treatment device 1, illustrated in FIG. 1, is implanted, fluid (e.g., aqueous humor) may be driven by a pressure gradient to flow through the channels and across the surface of plate structure 200.

In some embodiments, the channels 232 can include a ribbing pattern. The ribbing pattern and/or the geometry of the channels in the plate can be varied based on different severities of disease (e.g., mild, moderate, or severe glaucoma). In one embodiment, larger or smaller channels can be used to decrease intraocular pressure by different amounts. Changing intraocular pressure by a lower amount can decrease risk of hypotony (a condition that can exist if intraocular pressure is reduced too much) and increase efficacy at lowering pressure to a target level. In some embodiments, a device as described herein with smaller channels can decrease flow and decrease risk of hypotony. Likewise, larger channels can increase flow and allow the device to reduce intraocular pressure to a lower level.

The plate structure 200 may further comprise a first coating 280 applied to the first major surface 211 of the multi-directional plate 210. The first coating 280 may conform to the first topography of the first major surface 211 of the multi-directional plate 210. In other embodiments, the first coating 280 may form a topography that does not conform to the first topography of the first major surface 211 of the multi-directional plate 210.

The first coating 280 may have a thickness ranging from about 0.1 μm to about 10 μm or about 0.1 μm to about 2 μm—including all thickness and sub-ranges there-between. In one embodiment, the thickness is between about 0.4 μm (400 nm) and 0.6 μm (600 nm). In one embodiment, the thickness is about 0.4 μm (400 nm). In other embodiments, the thickness is between about 1 μm and about 5 μm, between about 1 μm and about 3 μm, between about 2 μm and about 5 μm, or between about 2 μm and about 4 μm. In one embodiment, the thickness is about 2 μm.

The plate structure 200 may further comprise a second coating 290 applied to the second major surface 212 of the multi-directional plate 210. The second coating 290 may conform to the plurality of surface features on the second major surface 212 of the multi-directional plate 210. In other embodiments, the second coating 290 may form a topography that does not conform to the second topography of the second major surface 212 of the multi-directional plate 210.

The second coating 290 may have a thickness ranging from about 0.1 μm to about 10 μm or about 0.1 μm to about 1 μm—including all thickness and sub-ranges there-between. In one embodiment, the thickness is between about 0.4 μm (400 nm) and 0.6 μm (600 nm). In one embodiment, the thickness is about 0.4 μm (400 nm). In other embodiments, the thickness is between about 1 μm and about 5 μm, between about 1 μm and about 3 μm, between about 2 μm and about 5 μm, or between about 2 μm and about 4 μm. In one embodiment, the thickness is about 2 μm.

In some embodiments, the plate structure 200 may comprise only the first coating 280—i.e., no second coating. In other embodiments, the plate structure 200 may comprise only the second coating 290—i.e., no first coating. In other embodiments, the plate structure 200 may comprise the first coating 280 and the second coating 290, whereby the first and second coatings overlap to fully encapsulate the multi-directional plate 210. In such embodiments, the side surface 203 of the plate structure 200 may comprise at least one of the first coating 280 and the second coating 290.

In some embodiments, the first and second coating, and any edge coating, can be thicker than the plate itself. In some embodiments, the coating thickness can be one, two or three orders of magnitude thicker than the plate structure. However, in other embodiments, the plate can be thicker than each coating or the additive thickness of the two coatings.

Coatings described herein can be applied by any suitable deposition method, such as but not limited to, physical vapor deposition, chemical vapor deposition, atomic layer deposition, spray coating, spin coating, self-assembly, dip coating, or brushing.

The first coating 280 may be applied to the first major surface 211 by any suitable deposition method. In a non-limiting example, the first coating 280 may be applied to the first major surface 211 by chemical vapor deposition, physical vapor deposition, or plasma-enhanced chemical vapor deposition. In another non-limiting example, the first coating 280 may be applied to the first major surface 211 by atomic layer deposition. In another non-limiting example, the first coating 280 may be applied to the first major surface 211 by spray coating. In another non-limiting example, the first coating 280 may be applied to the first major surface 211 by dip coating. In another non-limiting example, the first coating 280 may be applied to the first major surface 211 by brushing.

The second coating 290 may be applied to the second major surface 212 by any suitable deposition method. In a non-limiting example, the second coating 290 may be applied to the second major surface 212 by chemical vapor deposition, physical vapor deposition, or plasma-enhanced chemical vapor deposition. In another non-limiting example, the second coating 290 may be applied to the second major surface 212 by atomic layer deposition. In another non-limiting example, the second coating 290 may be applied to the second major surface 212 by spray coating. In another non-limiting example, the second coating 290 may be applied to the second major surface 212 by dip coating. In another non-limiting example, the second coating 290 may be applied to the second major surface 212 by brushing.

The first coating 280 may be the same as the second coating 290. The first coating 280 and the second coating 290 may be different. The first coating 280 may be hydrophilic. The first coating 280 may be hydrophobic. The first coating 280 may be lipophilic. The first coating 280 may be lipophobic. The second coating 290 may be hydrophilic. The second coating 290 may be hydrophobic. The second coating 290 may be lipophilic. The second coating 290 may be lipophobic. Each of the first and second coatings 280, 290 may independently be continuous. Each of the first and second coatings 280, 290 may independently be discontinuous. In some embodiments, the first and second coatings 280, 290 may both be hydrophobic. In some embodiments, the first and second coatings 280, 290 may both be hydrophilic. In some embodiments, the first and second coatings 280, 290 may both be lipophilic or lipophobic.

The first coating 280 may be organic. The first coating 280 may be inorganic. The second coating 290 may be organic. The second coating 290 may be inorganic.

In some embodiments, the first coating 280 is hydrophilic and the second coating 290 is hydrophobic. In some embodiments, the first coating 280 is hydrophilic and the second coating 290 is hydrophilic. Having at least one of the first and/or second coating 280, 290 be hydrophobic may help prevent the treatment device 1 from inadvertently sticking to tissue during implantation.

In some embodiments, a purpose of a first and/or second coating is to increase the toughness of the device. Also, a first and/or second coating can increase biocompatibility of the device and/or decrease scarring by decreasing tissue and/or fibroblast adhesion. In some embodiments, the coatings described herein are hydrophobic and decrease tissue adhesion. In some embodiments, tissue adhesion can be reduced by greater than about 10%, greater than about 60%, greater than about 70%, greater than about 80%, greater than about 90%, greater than about 95%, greater than about 96%, greater than about 97%, greater than about 98%, or greater than about 99% when compared to an uncoated plate.

In a non-limiting embodiment, the first and/or second coating may comprise a polymer, such as a parylene polymer (poly(para-xylylene)) or a derivative thereof. In other embodiments, the first and/or second coating can include aluminum oxide, a biocompatible film, a porous coating, or a lubricious coating. In one embodiment, the parylene polymer is a chlorine modified poly(para-xylylene), or a fluorine modified poly(para-xylylene). In one embodiment, the parylene polymer can be parylene C, parylene D, parylene N, a derivative thereof or a combination thereof. In other embodiments, the first and/or second coating can include aluminum oxide.

In other embodiments, other polymer(s) can be used in addition to, in combination with, or instead of a parylene polymer and/or aluminum oxide. In some embodiments, other polymeric materials can include, but are not limited to rubber, synthetic rubber, silicone polymers, thermoplastics, thermosets, polyolefins, polyisobutylene, acrylic polymers, ethylene-co-vinylacetate, polybutylmethacrylate, vinyl halide polymers (for example, polyvinyl chloride), polyvinyl ethers (for example, polyvinyl methyl ether), polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides (for example, Nylon 66 and polycaprolactam), alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene (for example, Teflon), poly(ether-ether-ketone), poly lactides such as PLA, PLGA, PLLA, derivatives thereof, or combinations thereof.

The resulting the treatment device 1 may comprise the first plurality of channels 222 present on the first exposed major surface 201 of the plate structure 200, wherein the first plurality of channels 222 are hydrophilic due to the presence of the first coating 280. The resulting treatment device 1 may comprise the second plurality of channels 232 present on the second exposed major surface 202 of the plate structure 200, wherein the second plurality of channels 232 are hydrophilic due to the presence of the second coating 290. As discussed, the hydrophilic channels may promote fluid flow through the channels after the treatment device 1 has been implanted into a subject's eye.

Referring to FIGS. 4, 5A, 5B, and 5C, generally, a treatment device 1001 is illustrated in accordance with another embodiment. The treatment device 1001 is similar to the treatment device 1 except as described herein below. The description of the treatment device 1 above generally applies to the treatment device 1001 described below except with regard to the differences specifically noted below. A similar numbering scheme will be used for the treatment device 1001 as with the treatment device 1 except that a "1000" series of numbering will be used.

The treatment device 1001 comprises a plate structure 1200 having a first exposed major surface 1201 that is opposite a second exposed major surface 1202. The plate structure 1200 may comprise a multi-directional plate 1210 comprising a first major surface 1211 opposite a second major surface 1212. The multi-directional plate 1210 may form a plurality of topographical features (for example, a repeating honeycomb pattern) on each of the first major surface 1211 and the second major surface 1212. Each of the first and second topographies may independently comprise a plurality of channels 1232 and/or a plurality of open-cells 1222.

Figure 5A:
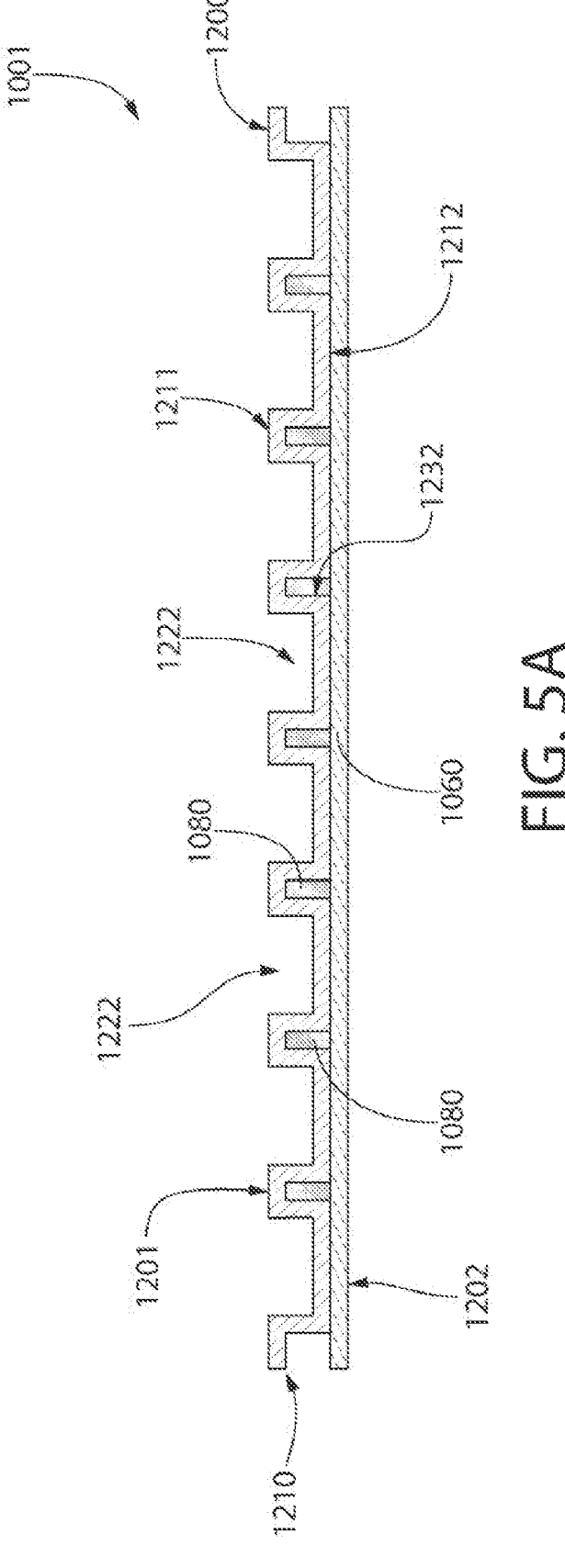
FIG. 5A is a portion of a cross-sectional view of section A of the device shown in FIG. 4 according to one embodiment.
Figure 5B:
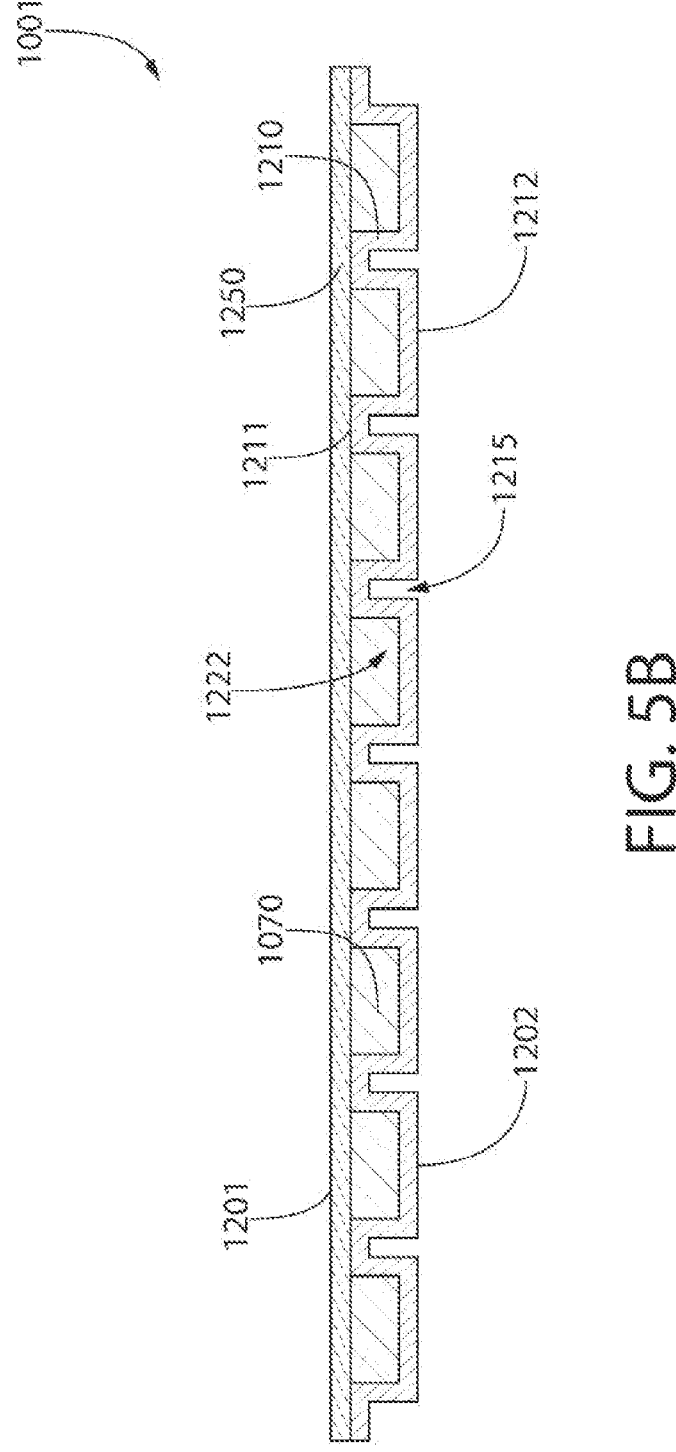
FIG. 5B is a portion of a cross-sectional view of section A of the device shown in FIG. 4 according to one embodiment.

Referring now to FIG. 5B, the plate structure 1200 may comprise a first delivery component 1070 present in the open voids created by the first topography formed by the first exposed surface 1211 of the multi-directional plate 1210. Specifically, the first delivery component 1070 may be present in the open voids created by the open-cells 1222 of first topography formed by the first major surface 1211 of the multi-directional plate 1210.

The first delivery component 1070 may comprise one or more active agents such as, but not limited to therapeutic and/or pharmacological components. The first delivery component 1070 may occupy some, all, or substantially all of the free volume present in the open-cells 1222 formed by the first topography.

In other embodiments, active agents can include any compound or drug having a therapeutic effect in a subject. Non limiting active agents include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, steroids, proteasome inhibitors, antibiotics, anti-inflammatories, anti-sense nucleotides, transforming nucleic acids, messenger ribonucleic acids, IOP lowering drugs, prostaglandins, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, cells, stem cells, liposomes, anti-metabolites such as mitomycin-C, combinations thereof, prodrugs thereof, pharmaceutical salts thereof, derivatives thereof, and the like.

The treatment device 1001 may further comprise a first coating 1050 applied to a first major surface 1211 of the multi-directional plate 1210. The first coating 1050 may cover both a first major surface 1211 of the multi-directional plate 1210 as well as a first delivery component 1070 that is present in the open-cells 1222 formed into the first major surface 1211 of the multi-directional plate 1210. The first coating 1050 may be in the form of a continuous film. The first coating 1050 may be flat. In other embodiments, the first coating 1050 may be conformal to the underlying pattern formed by the multi-directional plate 1210 and the first delivery component 1070.

Referring now to FIG. 5A, the plate structure 1200 may comprise a second delivery component 1080 present in the open voids created by the second topography formed by the second exposed surface 1212 of the multi-directional plate 1210. Specifically, the second delivery component 1080 may be present in the open voids created by the open-channels 1232 of the second topography formed by the second major surface 1212 of the multi-directional plate 1210. The second delivery component 1080 may be the same or different from the first delivery component 1070.

The second delivery component 1080 may comprise one or more therapeutic and/or pharmacological components—including but not limited to anti-inflammatory agents, steroids, antibiotics, analgesics. The second delivery component 1080 may occupy some, all, or substantially all of the free volume present in the channels 1232 formed by the first topography.

The treatment device 1001 may further comprise a second coating 1060 applied to a second major surface 1212 of the multi-directional plate 1210. The second coating 1060 may cover both the second major surface 1212 of the multi-directional plate 1210 as well as the second delivery component 1080 that is present in the open-channels 1232 formed into the second major surface 1212 of the multi-directional plate 1210. The second coating 1060 may be in the form of a continuous film. The second coating 1060 may be flat. In other embodiments, the second coating 1060 may be conformal to the underlying pattern formed by the multi-directional plate 1210 and the second delivery component 1080.

The second coating 1060 may be the same or different than the first coating 1050. For each of the first and the second coatings 1050, 1060, the resulting film may be formed from a slow-release material that dissolves slowly after exposure to aqueous humor or other biological fluids, thereby releasing the first delivery component 1070 from the channels 1232 of the treatment device 1001 after it has been implanted into a subject.

Figure 5C:
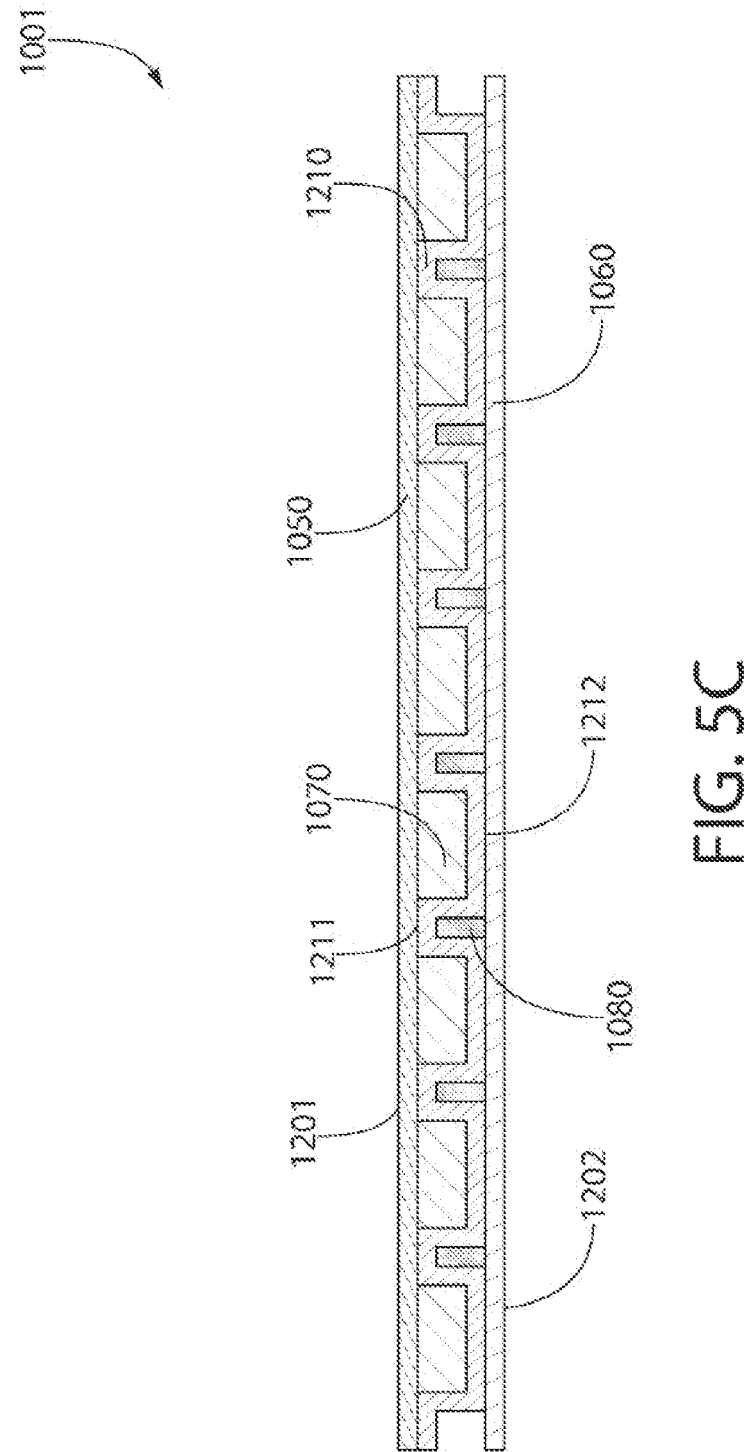
FIG. 5C is a portion of a cross-sectional view of section A of the device shown in FIG. 4 according to one embodiment.

Referring now to FIG. 5C, in other embodiments, the treatment device 1001 may comprise both the first and the second delivery components 1070, 1080, as well as the first and the second coatings 1050, 1060 to encapsulate the first and second delivery components 1070, 1080.

In other embodiments, the plate structure 1200 may comprise at least one of the first coating 1050 and/or the second coating 1060 without the presence of the first and/or second delivery components 1070, 1080. In such embodiments, the first coating 1050 and/or the second coating 1060 may form a film that covers the open cells 1222 and/or the open channels 1232 created by the multi-directional plate.

The presence of the films resulting from the first and/or the second coating 1050, 1060 may enhance the overall strength of the resulting treatment device. Specifically, layered structure(s) of the films formed by the first and second coatings 1050, 1060, which are bonded to the first and second major surfaces 1211, 1212 of the multi-directional plate 1210, provide added mechanical integrity to the resulting treatment device.

Beyond achieving the baseline flexibility to conform to curvature of the eye, the addition of the first and/or second coatings 1050, 1060 may provide a mechanism that allows the overall treatment device to match the elastic modulus of surrounding tissues (e.g., conjunctival and scleral tissues) to maximize biocompatibility or biointegration. Findings in brain implant research confirm that the flexibility of implants in soft tissue improves compliance of the implant with microscale movements of surrounding tissue and reduces tissue displacement and trauma as well as facilitates implantation of the treatment device.

Treatment Device Insertion Embodiment

Figure 6:
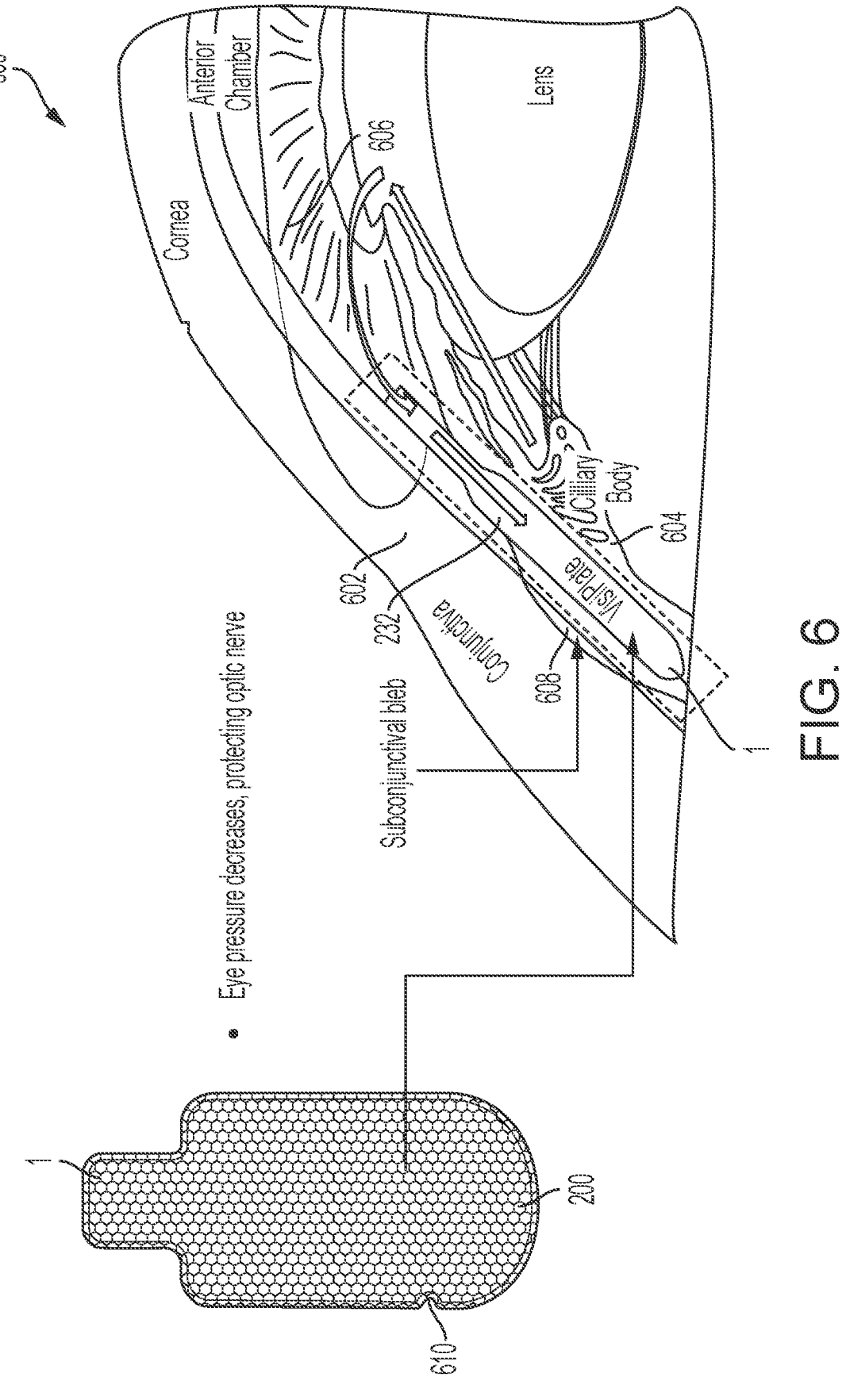
FIG. 6 is a diagram of a treatment device implanted in the anterior chamber and between conjunctival tissue and scleral tissue of a patient's eye, according to an example embodiment of the present disclosure.

FIG. 6 is a diagram of the treatment device 1 implanted between conjunctival tissue 602 and scleral tissue 604 of a patient's eye 600, according to an example embodiment of the present disclosure. The treatment device 1 is a biocompatible ocular implant that includes a thin, flexible plate to facilitate safe, comfortable, and effective treatment. The treatment device 1 includes a plate structure 200 having a plurality of channels 232. The example channels 232 are configured to facilitate the draining of accumulated aqueous in the anterior chamber 606 of the eye 600 to a pocket (bleb) 608 that is located between the conjunctival tissue 602 and scleral tissue 604. This enables intraocular pressure from the accumulation of the aqueous in the anterior chamber 606 to be reduced. The removed aqueous in the pocket 608 is gradually reabsorbed by surrounding tissue, which enables further accumulating aqueous to be removed from the anterior chamber 606. This continuous draining of aqueous (e.g., glaucoma drainage) lowers pressure within the eye 600 and protects the optic nerve. The redundant channels 232 of the plate structure 200 prevent single-end clogging by scar tissue. Further, the thin profile of the plate structure 200 hinders tissue erosion.

FIG. 6 also shows the plate structure 200 including a notch 610 along a perimeter. While the notch 610 is shown on a lower left section of the plate structure 200, it should be appreciated that the notch 610 may be located at any location of the perimeter. Further, while one notch 610 is shown, the plate structure 200 may include two or more notches. The notch 610 is configured to facilitate proper installation and placement of the plate structure 200 within a patient's eye. The notch 610 may be indicative as to whether the channels 232 of the plate structure 200 are aligned upwards or downwards. The notch 610 accordingly provides confirmation to a clinician that the plate structure 200 is properly orientated.

Figure 7:
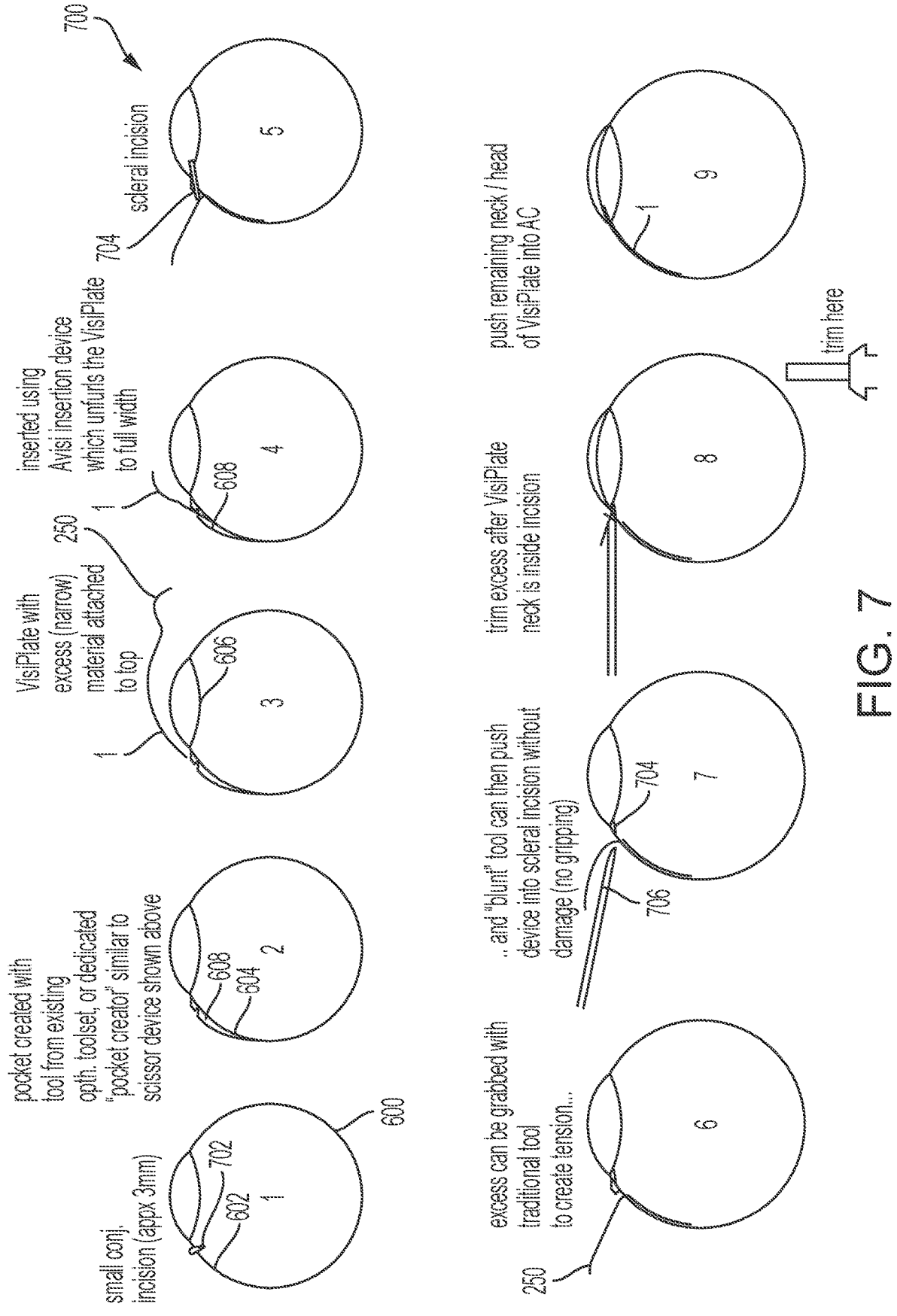
FIG. 7 is a diagram of the treatment device for a treatment application, according to an example embodiment of the present disclosure.

FIG. 7 is a diagram of an example insertion procedure 700 for the treatment device 1, according to an example embodiment of the present disclosure. It should be appreciated that the example procedure 700 is exemplary, and that additional, fewer, or different steps may be performed, as described below in relation to different types of insertion tools. At Event (1), a small incision 702 is made in the conjunctival tissue 602. The incision 702 may have a length between 1 mm and 5 mm, preferably around 3 mm and may be made via a scalpel. At Event (2), a pocket 608 is formed between the conjunctival tissue 602 and scleral tissue 604. In some embodiments, the pocket 608 is formed using the insertion tool described herein.

At Event (3), the treatment device 1 is brought into proximity of the patient's eye 600. The treatment device 1 may include an extension portion 250 with excess material that enables its length to be customized for reaching the anterior chamber 606 of the patient's eye 600. In some embodiments, the treatment device 1 is furled or otherwise placed into an insertion position around or within an insertion tool. At Event (4), the insertion tool is inserted into the pocket 608 and unfurls or otherwise deploys the treatment device (1). The insertion tool is then removed leaving the treatment device unfurled within the pocket 608.

At Event (5), a small incision 704 is made into the scleral tissue using a scalpel. The incision 704 may have a diameter or width between 1 mm and 4 mm, preferably around 2 mm. At Event (6), a tool, such as tweezers or pliers, grabs an end of the extension portion 250 to create tension. A blunt tool 706 is then used in Event (7) to push at least a portion of the extension portion 250 into the scleral incision 704. At Event (8), any excess of the extension portion 250 is removed or trimmed. Then at Event (9), the remaining extension portion 250 is pushed into the anterior chamber 606, thereby fully inserting the treatment device 1. In some embodiments, the incisions 702 and 704 may be sutured or otherwise closed.

Figure 8A:
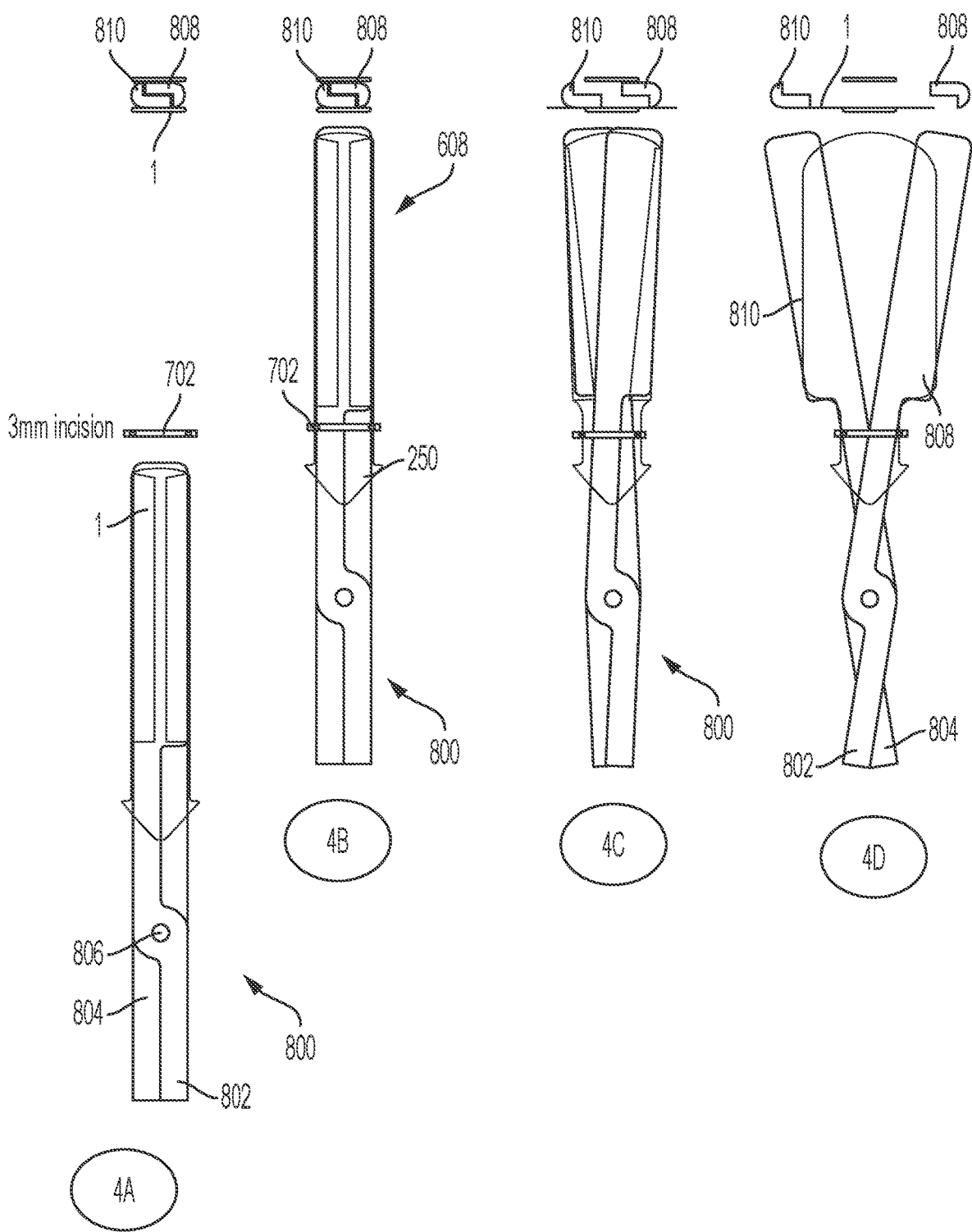
FIGS. 8A and 8B are diagrams showing how an insertion tool is used to insert the treatment device, according to an example embodiment of the present disclosure.
Figure 8B:
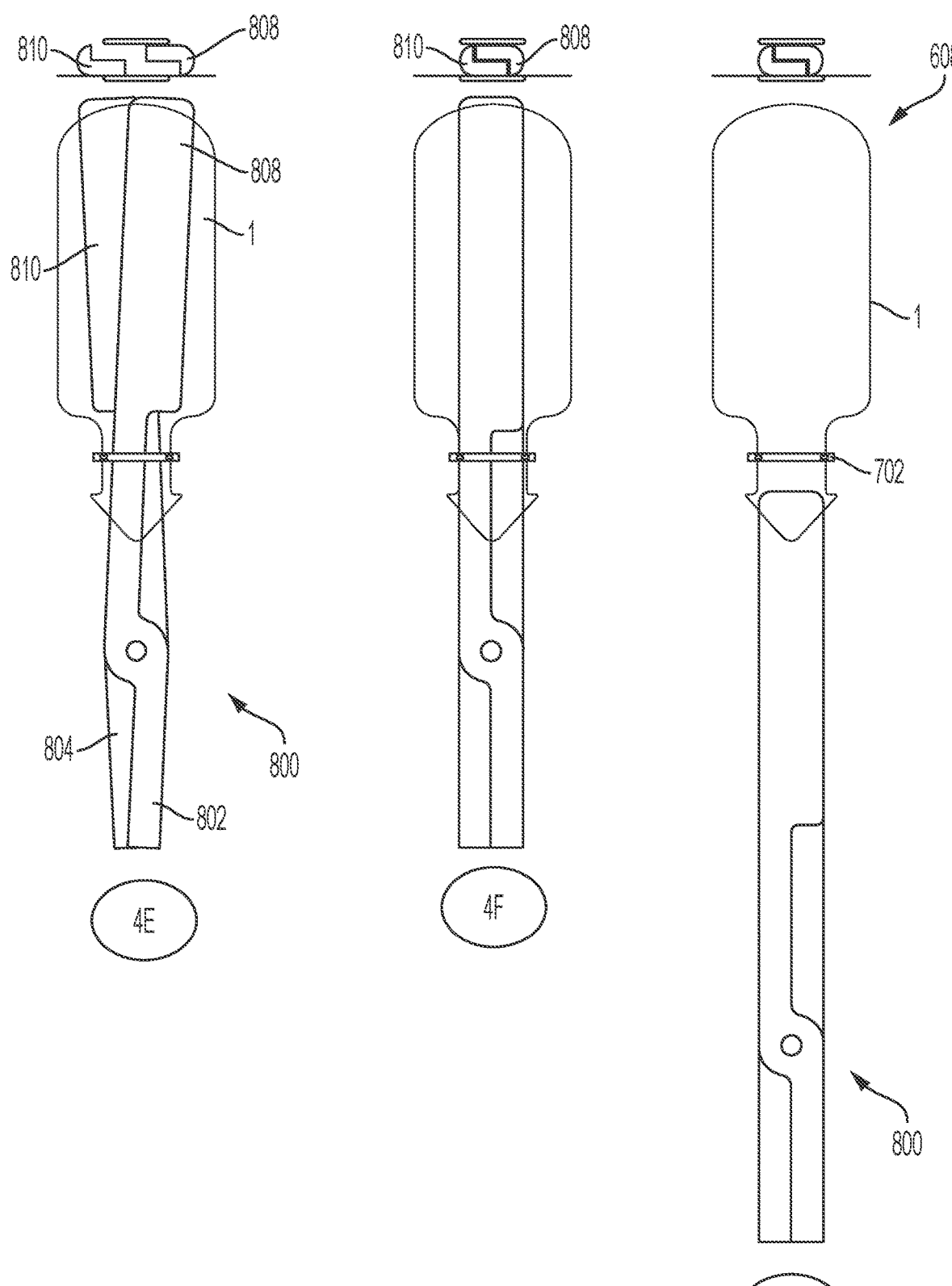

FIGS. 8A and 8B are diagrams showing how an insertion tool 800 is used to insert the treatment device 1, according to an example embodiment of the present disclosure. At shown in the illustrated example, the insertion device 800 is a scissoring mechanism that has a first arm 804 and a second arm 804 connected together at a pivot point 806. A first end 808 (e.g., a first prong) of the first arm 802 has an L-shape to interlock with a first end 810 (e.g., a second prong) of the second arm 804 (shown in a cross-section diagram of the insertion device 800). When the first end 808 of the first arm 802 is interlocked with the first end 810 of the second arm 804, the insertion tool 800 has an ovular profile with a diameter of around 2 to 3 mm, which enables insertion through the incision 702. Opposite ends of the first arm 802 and the second arm 804 may include handles to enable a clinician to rotate the arms 802 and 804 about the pivot point 806.

At Event (4A) of FIG. 8A (corresponding to Event (4) of FIG. 7), the treatment device 1 is wrapped or furled around the closed ends 808 and 810 of the arms 802 and 804. The ovular shape of the ends 808 and 810 facilitates the folding of the treatment device 1 around the insertion tool 800. At Event (4B), the insertion tool 800 is inserted through the incision 702 into the pocket 608. During this action, the arms 802 and 804 are kept in a closed position to keep the treatment device 1 furled. In this example, the extension portion 250 has an arrow-shape with sides that extend past a length of the incision 702. The shape and width of the extension portion 250 provides stop that prevents the insertion tool 800 from being inserted too far into the pocket 608.

At Event (4C) after a leading section of the insertion tool 800 is fully inserted, the arms 802 and 804 are rotated about the pivot point 806. This causes the ends 808 and 810 to separate from each other, thereby causing the treatment device 1 to begin to unfurl. At Event (4D), the arms 802 and 804 are further rotated to a maximum rotation point. This causes the treatment device 1 to completely unfurl to a flat plate. As shown, the ends 808 and 810 include surfaces that are flat, which causes the treatment device 1 to be spread flat. Further, edges of the ends 808 and 810 may be blunt to provide for dissection of the conjunctival tissue 602 and scleral tissue 604 to further form the pocket 608. Also, as shown in FIG. 8, the insertion tool 800 is inserted into the incision 702 close enough to the pivot point 806 such that rotation of the arms 802 and 804 does not exceed a length of the incision 702.

At Event (4E), after the treatment device 1 is spread into a flat plate, the arms 802 and 804 are rotated back to a closed position. This causes the ends 808 and 810 to reengage such that the separate L-profiles interlock to form an ovular profile, as shown in Event (4F) when the arms 802 and 804 are fully in a closed position. At Event (4G), the insertion tool 800 is removed from the pocket 608 through the incision 702, leaving the treatment device 1 in place. The use of the insertion tool 800 enables a treatment device 1 with a diameter wider than an incision 702 to be placed into a pocket 708 between the conjunctival tissue 602 and scleral tissue 604.

Figure 9:
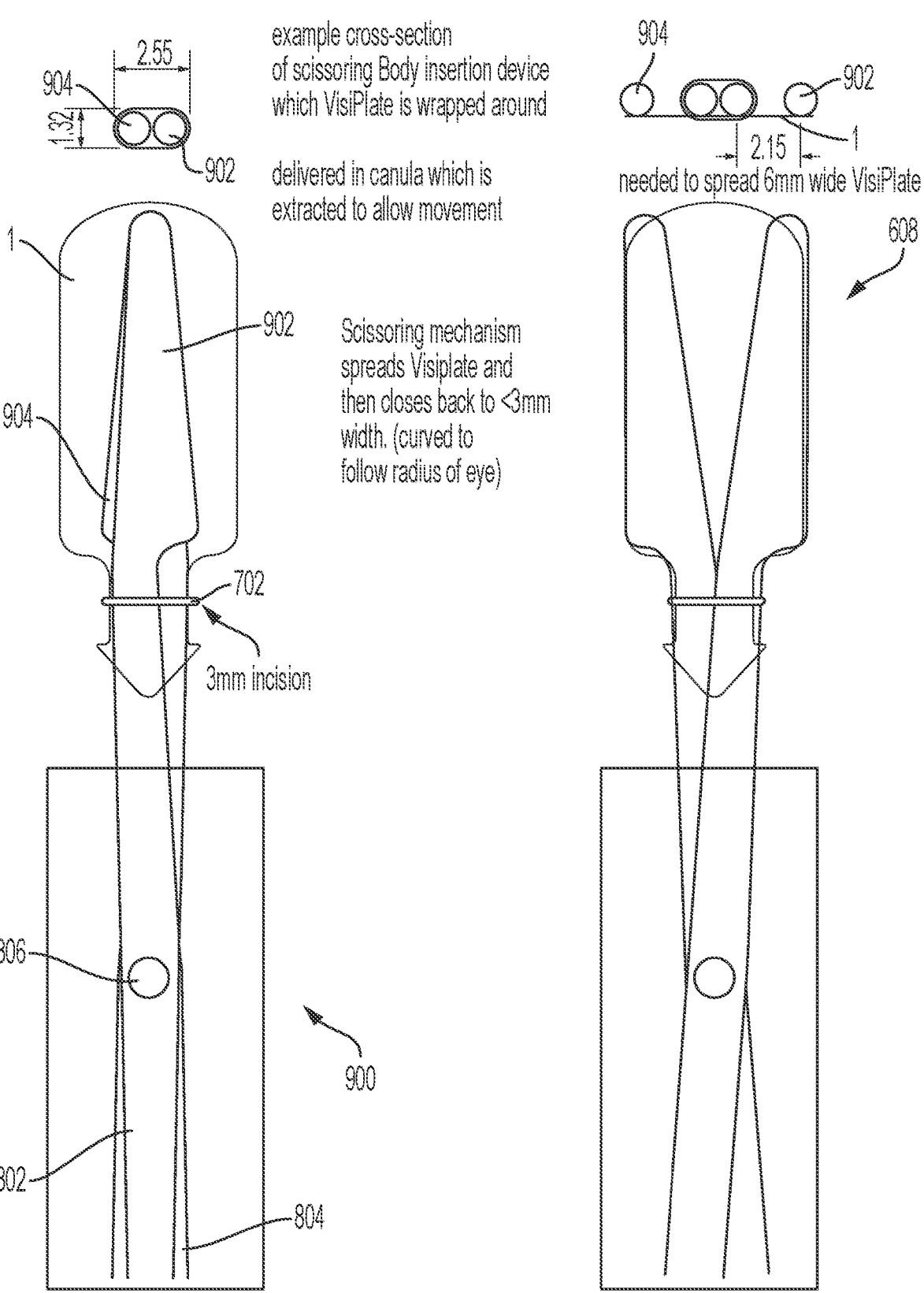
FIG. 9 is a diagram of an alternative insertion tool, according to an example embodiment of the present disclosure.

FIG. 9 is a diagram of an alternative insertion tool 900, according to an example embodiment of the present disclosure. In this example, the first arm 802 includes a first prong 902 and the second arm 804 includes a second prong 904. In this example, the prongs 902 and 904 each have a circular profile with a diameter of about 1.3 mm. Together, the insertion tool 900, including the prongs 902 and 904 in a closed position, has a width of about 2.5 mm, which is less than the 3 mm incision 702. In a closed position, the treatment device 1 is wrapped around the prongs 902 and 904.

The example prongs 902 and 904 in this embodiment have a triangular shape with a rounded leading edge, a radiused edge, or a blunted leading edge. Since a base of the triangular side moves less when the arms 802 and 804 are opened, the extra material still spreads over the treatment device 1. By contrast, the leading edge of the prongs 902 and 904 have more movement that cover the width of the treatment device 1, which enables the prongs 902 and 904 to have a smaller width in this area. In other words, a width of the prongs 902 and 904 is tapered to account for increased amounts of coverage for sections of the prongs 902 and 904 further from the pivot point 806. In this embodiment, the prongs 902 and 904 are shaped to match a shape of the unfurled treatment device 1. In another example, the prongs 902 and 904 are taped to match a treatment device 1 that has a wedge-shape or sides that are not parallel. Such a configuration enables the prongs 902 and 904 to bluntly dissect the subconjunctival pocket or space and cause the treatment device 1 to unfurl and lay flat.

In some embodiments, the prongs 902 and 904 are configured to expand to a predefined geometry that is greater than a surface of the unfurled treatment device 1. Having the prongs 902 and 904 expand to a predefined geometry that is greater than the treatment device 1 facilitates aqueous absorption and/or makes the treatment device 1 easier to unfurl. The prongs 902 and 904 may expand a distance that is at least 0.5 mm greater than a width of the treatment device 1, for example.

In some embodiments, the prongs 902 and 904 are inserted inside of a cannula (not shown) for insertion through the incision 702. In these embodiments, the cannula is removed through the incision 702, thereby enabling the arms 802 and 804 to move to an open position, causing the prongs 902 and 904 to spread the treatment device 1 within the pocket 608. The use of the cannula prevents the arms 802 and 804 from inadvertently opening during insertion of the tool 900. Further, the cannula may prevent the prongs 902 and 904 and/or the wrapped treatment device 1 from snagging edges of the conjunctival tissue 602 and scleral tissue 604 at the incision location during insertion. Further, the cannula helps prevent the treatment device 1 from being dislodged during delivery into the pocket 608.

Figure 10:
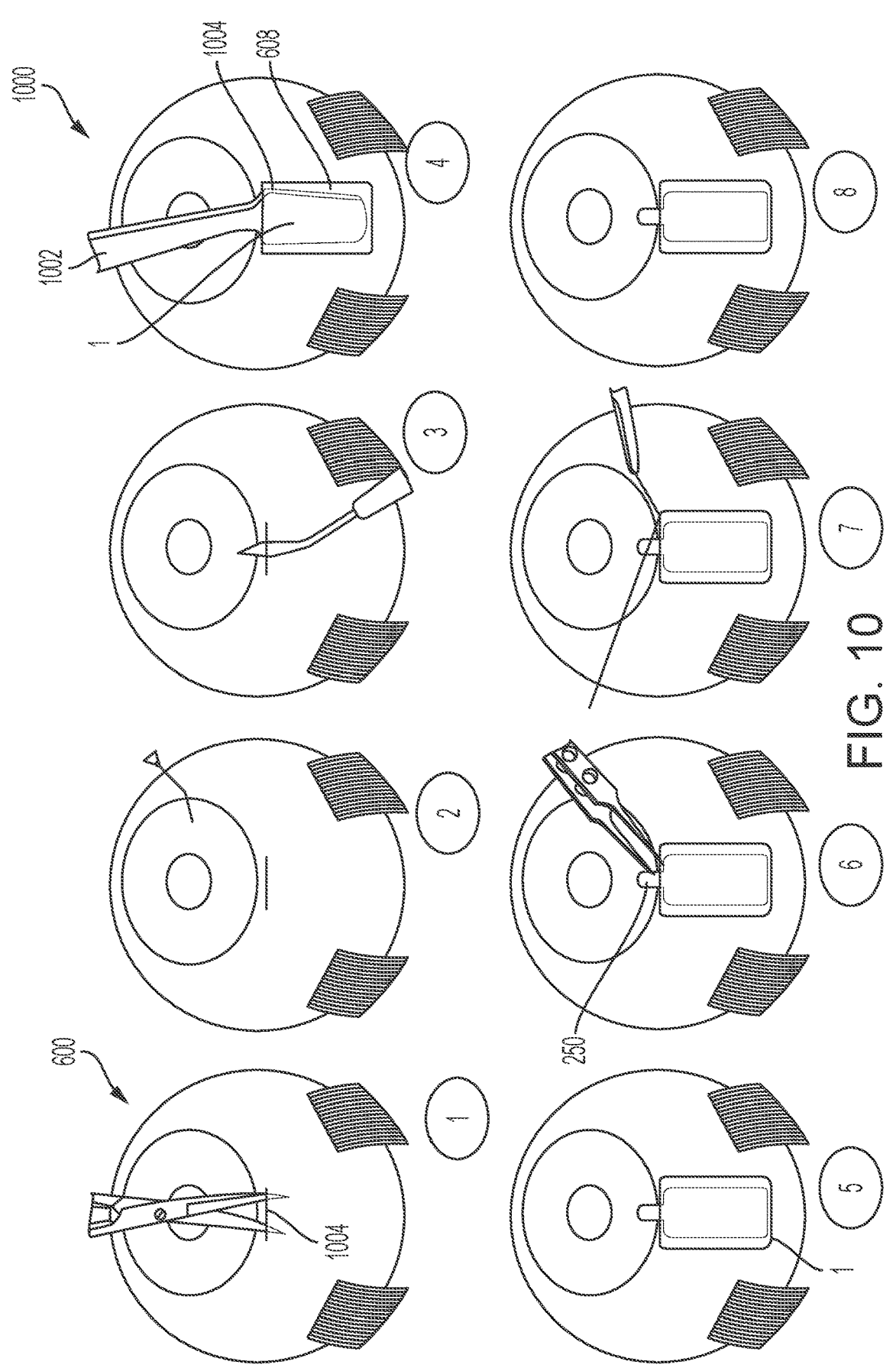
FIG. 10 is a diagram of a procedure for inserting the treatment device using another type of insertion tool, according to an example embodiment of the present disclosure.

FIG. 10 is a diagram of a procedure 1000 for inserting the treatment device 1 using another type of insertion tool 1002, according to an example embodiment of the present disclosure. At Event (1), a cutting tool pierces the conjunctival tissue of a patient's eye with a sharp end. The tool opens, causing sharp edges to form an incision 1004. At Event (2), a fluid is added to an anterior chamber of the patient's eye to inflate the cornea. At Event (3), another tool makes an incision into the scleral tissue for access into the anterior chamber.

At Event (4), the insertion tool 1002 with a furled treatment device 1 is inserted into the incision 1004. In this example, the insertion tool 1002 is sliding mechanism with blunt, slightly curved prongs. Compared to the prongs 902 and 904 of FIG. 9, the prongs of FIG. 10 are wider but still able to fit through the incision 1004. Here, the treatment device 1 is clasped between the two prongs. A top prong faces the conjunctiva tissue and is configured to slide forward to push the treatment device 1 off of the bottom prong, thereby sliding the treatment device 1 into the sub-conjunctival space or pocket 608. After the treatment device 1 is pushed off of the prongs, the prongs are used in a sweeping motion to tamp down the treatment device 1 in the pocket 608, thereby ensuring the treatment device 1 lays flat. Event (5) shows the treatment device 1 lying flat within the pocket 608 with the insertion tool 1002 removed.

At Event (6), another tool grasps the extension portion 250 of the treatment device 1 for placement through the second incision into the anterior chamber, thereby forming a fluid pathway to the pocket 608 to relieve pressure within the anterior chamber. At Event (7) one or more sutures are placed to close the incisions. At Event (8), the sutures are completed, thereby completing the procedure 1000 to insert the treatment device 1.

Figure 11:
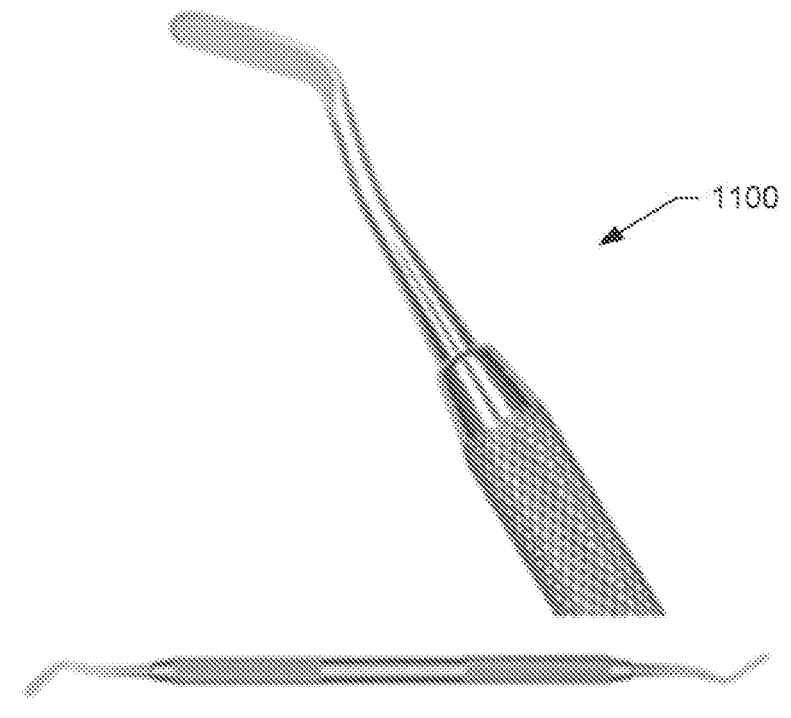
FIG. 11 is a diagram of another insertion tool, according to an example embodiment of the present disclosure.

FIG. 11 is a diagram of another insertion tool 1100, according to an example embodiment of the present disclosure. In this example, the insertion tool 1100 includes a blunt, 1.5 mm wide prong. The example prong is configured to guide the treatment device 1 through a scleral incision into an anterior chamber of a patient's eye. In some embodiments, the insertion tool 1100 may be slightly curved and have a broad spatula-like prong that is used like a sheath glide to slide the treatment device 1 into the sub-conjunctival space or pocket 608. The insertion tool 1100 may be moved in a side-to-side sweeping motion across the treatment device 1 to ensure the treatment device 1 lays flat. In some embodiments, the prong of the insertion tool 1100 may have a surface area that is between 5 mm×10 mm to 8 mm×11 mm. In these examples, a longer or wider incision may be needed.

Figure 12:
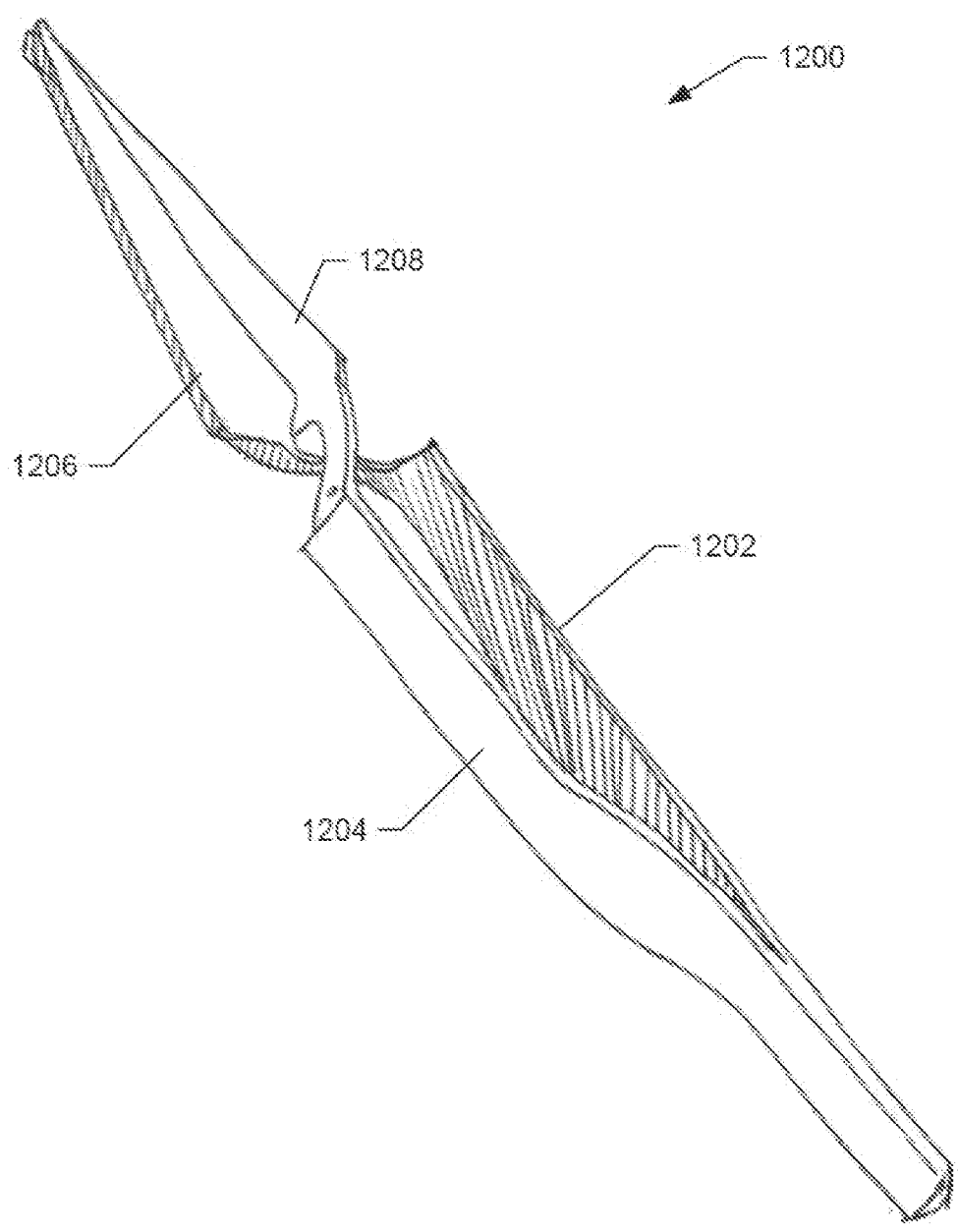
FIG. 12 is a diagram of another insertion tool with an expandable mechanism, according to an example embodiment of the present disclosure.

FIG. 12 is a diagram of another insertion tool 1200, according to an example embodiment of the present disclosure. The insertion tool 1200 includes an expandable mechanism that includes a first arm 1202 and a second arm 1204. The first and second arms 1202 and 1204 are bent inward to cross each other. A first end 1206 of the first arm 1202 contacts a second end 1208 of the second arm 1204 when the insertion tool 1200 is in a resting position. The first end 1206 and the second end 1208 may include flat surfaces that enable insertion through an incision made in a patient's eye to a sub-conjunctival space or pocket. The first end 1206 and the second end 1208 together have a width that is less than 5 mm, for example, and a height that is less than 1 mm, for example.

Opposite ends of the first and second arms 1202 and 1204 are connected together. Additionally, the arms 1202 and 1204 are angled or bent with respect to each other. The connection and angling of the arms 1202 and 1204 creates a spring force that pushes the ends 1206 and 1208 together. An operator may apply pressure by pressing against the spring force by pressing the first arm 1202 towards the second arm 1204. The applied pressure causes the first end 1206 and the second end 1208 to separate in opposite directions. This movement in opposite directions causes a furled treatment device 1 to be opened into a flat plate.

In an example, the treatment device 1 may be furled around the first end 1206 and the second end 1208 of the insertion tool 1200. After insertion, pressure is applied to the arms 1202 and 1204, causing the ends 1206 and 1208 to move apart and unfurl the treatment device 1. After unfurling the treatment device 1, pressure on the arms 1202 and 1204 is relaxed, enabling the ends 1206 and 1208 to come back together. The ends 1206 and 1208 may then be removed from sub-conjunctival space or pocket.

It should be appreciated that the above insertion tools may be coated with a hydrophobic coating, which may include Teflon, to lower friction between the tools and facilitate their insertion/removal from a surgical site.

Treatment Device Reinforcement Embodiment

Figure 13:
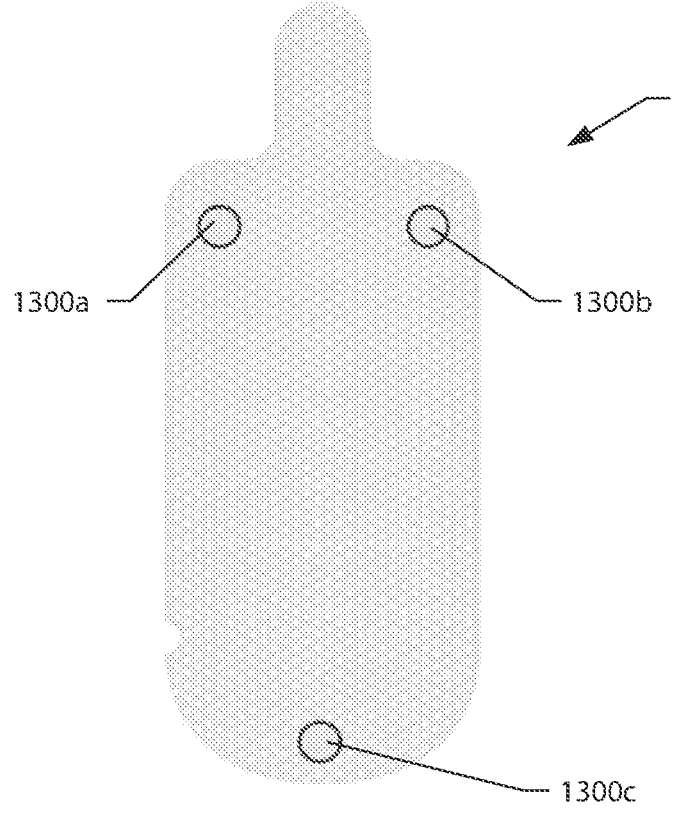
FIG. 13 is a diagram of the treatment device with holes or apertures for reinforcement to prevent bending or folding after implantation, according to an example embodiment of the present disclosure.

In some embodiments, the plate structure 200 of the treatment device 1 includes one or more holes or apertures for reinforcement. As described above, the treatment device 1 may be foldable for insertion. However, after unfolding, the treatment device 1 may retain some internal compressive forces that cause at least edges to bend. To prevent any bending, one or more holes or apertures 1300 may be added, as shown in FIG. 13.

The example holes 1300 may be formed via a laser during a manufacturing process. A ring of thicker parylene or alumina may be placed around an edge of the holes 1300 for reinforcement. Tissue glue may then be applied on one side and/or within the holes 1300. The glue hydrates upon the treatment device 1 being inserted/implanted into a patient's eye. Once hydrated, the glue anchors the treatment device 1 to the scleral tissue in the sub-conjunctival space or pocket 608, thereby preventing bending or lateral movement.

CONCLUSION

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific example embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Example embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention is claimed as follows:

1. A system for lowing intraocular pressure, the system comprising:
   an insertion tool including:
      a first arm connected to a second arm at a pivot point forming a scissoring mechanism;
      a first prong connected to a first end of the first arm; and
      a second prong connected to a first end of the second arm,
         wherein the first and second prongs are configured to have a combined dimension that is less than a length of an incision of conjunctival tissue of a patient's eye when the first and second arms are in a closed position, and wherein the first and second arms are configured to be actuated to an open position after the first and second prongs are inserted into a pocket formed between the conjunctival tissue and scleral tissue of the patient's eye, wherein actuation to the open position causes the first and second prongs to separate and increase a width of the pocket; and a treatment device configured to furl or wrap around the first and second prongs when the first and second arms are in a closed position, wherein the first and second prongs are configured to cause the treatment device to unfurl or spread to a flat shape in the pocket when the first and second arms are actuated to the open position.

2. The system of claim 1, wherein the first and second prongs have at least a flat side to spread out the treatment device to the flat shape.

3. The system of claim 1, wherein the first and second prongs are configured to at least one of overlap or interlock when the first and second arms are in the closed position.

4. The system of claim 1, wherein the treatment device includes:

a foldable plate comprising a first surface opposite a second surface, wherein the first surface includes a series of fluid channels;

a first coating on the first surface; and a second coating on the second surface, wherein the fluid channels form a geometric pattern with each channel having a height and first width to produce a desired fluid flow rate.

5. The system according to claim 4, wherein the foldable plate includes an extension portion for placement within an anterior chamber of the patient's eye, and wherein the fluid channels include a plurality of open-ended channels interconnected to form an intersecting network of fluid pathways.

6. The system of claim 1, wherein the first and second prongs have at least one of a radiused edge or a blunted leading edge.

7. The system of claim 1, wherein the first and second prongs are shaped to match a shape of the unfurled treatment device.

8. The system of claim 1, wherein the first and second prongs are configured to expand to a predefined geometry that is greater than a surface of the unfurled treatment device.

9. The system of claim 1, wherein a cannula is provided over the first and second prongs to retain the furled treatment device during insertion into the pocket formed between the conjunctival tissue and scleral tissue of the patient's eye.

10. The system of claim 1, further comprising:

a first handle connected to a second end of the first prong; and a second handle connected to a second end of the second prong.

11. An insertion tool for a device that lowers intraocular pressure, the insertion tool comprising:

a first arm having a first end and a second end; and a second arm having a first end and a second end, the second end of the second arm being connected to or integrally formed with the second end of the first arm, wherein the first arm and the second arm are bent or angled with respect to each other forming an expandable mechanism such that a first end of the first arm contacts the first end of the second arm when external force is absent, wherein the first ends of the first and second arms are configured to have a combined dimension that is less than a length of an incision of conjunctival tissue of a patient's eye when the first and second arms are in a closed position, and wherein the first and second arms are configured to be actuated to an open position after the first ends of the first and second arms are inserted into a pocket formed between the conjunctival tissue and scleral tissue of the patient's eye, wherein actuation to the open position causes the first ends to separate and increase a width of the pocket.

12. The insertion tool of claim 11, wherein the first end of the first arm and the first end of the second arm include flat surfaces.

13. The insertion tool of claim 11, wherein a treatment device is furled or wrapped around the first and second ends when the first and second arms are in a closed position, and wherein the first and second ends are configured to cause the treatment device to unfurl or spread to a flat shape in the pocket when the first and second arms are actuated to the open position.

14. The insertion tool of claim 13, wherein the treatment device includes:

a foldable plate comprising a first surface opposite a second surface, wherein the first surface includes a series of fluid channels;

a first coating on the first surface; and a second coating on the second surface, wherein the fluid channels form a geometric pattern with each channel having a height and first width to produce a desired fluid flow rate.

15. The insertion tool of claim 11, wherein the first and second arms include a hydrophobic coating.

16. A method of inserting a treatment device to lower intraocular pressure, the method comprising:

causing the treatment device to wrap around two prongs or ends of an expandable mechanism when the two prongs or ends are in a closed position;

causing an incision to be made in conjunctival tissue of a patient's eye;

causing the two prongs to go through the incision forming a pocket between the conjunctival tissue and scleral tissue of the patient's eye, an extension portion of the treatment device protruding from the incision;

causing the two prongs to separate to an open position, thereby causing a width of the pocket to widen and causing the treatment device to unwrap to a flat sheet within the pocket;

causing the two prongs to move to the closed position; and causing the two prongs of the expandable mechanism to be removed from the pocket through the incision, wherein a diameter of the two prongs and the wrapped treatment device is less than a diameter of the incision.

17. The method of claim 16, further comprising:

causing a second incision to be made into the scleral tissue to provide access to an anterior chamber of the patient's eye; and causing the extension portion of the treatment device to be placed into at least a portion of the anterior chamber, thereby forming a fluid pathway between the anterior chamber and the pocket between the conjunctival tissue and scleral tissue of the patient's eye.

18. The method of claim 16, further comprising suturing the incision after removal of the two prongs.

19. The method of claim 16, further comprising:

forming at least one suture hole on the treatment device using a laser; and reinforcing the at least one suture hole.

20. The method of claim 19, further comprising:

causing tissue glue to be placed within the at least one suture hole; and after the treatment device unwraps, causing the tissue glue to anchor the treatment device to the scleral tissue.

\*    \*    \*    \*    \*